United States Patent
Qi et al.

(10) Patent No.: US 11,389,503 B2
(45) Date of Patent: Jul. 19, 2022

(54) COMPOSITION COMPRISING AN ALGAL PROTEOGLYCAN EXTRACT AND USE THEREOF

(71) Applicants: Qing Qi, Beijing (CN); Jian Ding, Shanghai (CN)

(72) Inventors: Qing Qi, Beijing (CN); Jian Ding, Shanghai (CN)

(*) Notice: Subject to any disclaimer, the term of this patent is extended or adjusted under 35 U.S.C. 154(b) by 103 days.

(21) Appl. No.: 16/922,567

(22) Filed: Jul. 7, 2020

(65) Prior Publication Data
US 2020/0360470 A1 Nov. 19, 2020

Related U.S. Application Data

(62) Division of application No. 16/071,020, filed as application No. PCT/CN2017/071861 on Jan. 20, 2017, now Pat. No. 10,729,743.

(30) Foreign Application Priority Data
Jan. 20, 2016 (CN) .......... 201610037244.6

(51) Int. Cl.
| | |
|---|---|
| *A61K 36/02* | (2006.01) |
| *A61K 38/16* | (2006.01) |
| *A61P 35/00* | (2006.01) |
| *A61K 9/00* | (2006.01) |
| *A61K 31/282* | (2006.01) |
| *A61K 31/513* | (2006.01) |
| *A61K 31/675* | (2006.01) |
| *A61K 31/704* | (2006.01) |
| *A61K 31/7048* | (2006.01) |
| *A61K 35/748* | (2015.01) |
| *A61K 45/06* | (2006.01) |

(52) U.S. Cl.
CPC .......... *A61K 38/164* (2013.01); *A61K 9/0019* (2013.01); *A61K 9/0053* (2013.01); *A61K 31/282* (2013.01); *A61K 31/513* (2013.01); *A61K 31/675* (2013.01); *A61K 31/704* (2013.01); *A61K 31/7048* (2013.01); *A61K 35/748* (2013.01); *A61K 36/02* (2013.01); *A61K 45/06* (2013.01); *A61P 35/00* (2018.01)

(58) Field of Classification Search
CPC .................................................... A61K 36/02
See application file for complete search history.

(56) References Cited

U.S. PATENT DOCUMENTS

| | | | |
|---|---|---|---|
| 5,709,855 A | 1/1998 | Bockow | |
| 6,893,642 B1 | 5/2005 | Qi et al. | |

FOREIGN PATENT DOCUMENTS

| | | |
|---|---|---|
| CN | 1280855 A | 1/2001 |
| CN | 1098707 C | 1/2003 |
| EP | 1197218 A1 | 4/2002 |

(Continued)

OTHER PUBLICATIONS

Talero, E. et al., "Bioactive Compounds Isolated from Microalgae in Chronic Inflammation and Cancer"; Marine Drugs (2015); vol. 13; pp. 6152-6209.

(Continued)

*Primary Examiner* — Rosanne Kosson
(74) *Attorney, Agent, or Firm* — Fox Rothschild LLP

(57) ABSTRACT

The present application provides use of an algal proteoglycan extract and a composition comprising the same in treating or preventing tumor, pain, inflammation or diseases mediated by inflammatory factors.

18 Claims, 2 Drawing Sheets

(56) References Cited

FOREIGN PATENT DOCUMENTS

| JP | 2003-504410 A | 2/2003 |
| JP | 2005318878 A | 11/2005 |
| WO | 9639829 A1 | 12/1996 |

OTHER PUBLICATIONS

Zhu, D. et al., "Application of Spirulina Capsules in the Treatment of Middle and Late Stage Malignant Tumors"; Proceeding of Clinical Medicine (2010); vol. 19:No. 7B, pp. 948-949 (English Abstract).

Qin, L. et al., "Application of Several Common Algae in Tumor Treatment"; Journal of Youjiang Medical University for Nationalities (2013); vol. 5, pp. 684-686 (English Abstract).

Zheng, W. et al., "Organic selenium compounds from plants: their chemistry and applications in medicine" Jinan University Press (2001); p. 257.

Li, Y. et al., "Process in Polysaccharide of Spirulina Platensis for Antitumore," Clincial Focus (Jan. 20, 2011); 26(2):170-172.

Deng, R. et al., "Hypolipidemic, Antioxidant, and Antiinflammatory Activities of Microalgae Spirulina," Cardiovascular Therapeutics (2010); 28:e33-e45.

Sheng, Y. et al., "Experimental Process in Polysaccharide of Spirulina Platensis for Antitumor," Jiangsu Journal of Traditional Chinese Medicine (Dec. 31, 2005); 26(8):56-58.

Guan, Y. et al., "The Influence of Polysaccharide of Spirulina Platensis on Inhibition Activity of Immobilized Phycocyanin Against Caner Cells Growth," Acta Nutrimenta Sinica (Sep. 30, 2002); 24(3):252-255.

Wang, F. et al., "Flocculation Process During Extraction of Water-soluble Polysaccharides from Spirulina," The Chinese Journal of Process Engineering (Jun. 30, 2011); 11(3):468-474.

Xu, G. et al., "Application of tyrosine kinase inhibitors in the treatment of pancreatic cancer," Foreign Med. Sci.: Digive System (2005); 25(1):51-54.

Konícková, R. et al., "Anti-cancer effects of blue-green alga *Spirulina platensis*, a natural source of bilirubin-like tetrapyrrolic compounds," Annals of Hepatology (2014); 13(2):273-283.

Durand-Chastel, H., "Production of Spirulina biomass rich in gamma-linolenic acid and sulfolipids," Bulletin de l'Institut océanographique de Monaco (1999); 19:541-546.

Bobadilla, F. et al., "Soluble ß-1,3/1,6-glucan in seaweed from the southern hemisphere and its immunomodulatory effect," Carbohydrate Polymers (2013); 92:241-248.

Pomin, V. H. et al., "Sulfated glycans in inflammation," European Journal of Medicinal Chemistry (2015); 92:353-369.

Aravindan, S. et al., "Anti-Pancreatic Cancer Deliverables from Sea: First-Hand Evidence of the Efficay, Molecular Targets and Mode of Action for Multifarioius Polyphenols from Five Different Brown-Algae," PLOS (Apr. 2013); 8: e61977 (15 pages).

Ponomaryov, V.D., Extraction of Drug Raw Materials. Moscow, Meditsina, 1976, 202 p.

Sakata, Y. et al., "A Late Phase II Study of CPT-11 Irinotecan Hydrochloride, in Patients with Advanced Pancreatic Cancer"; Japanese Journal of Cancer and Chemotherapy (1994); vol. 21:7; pp. 11 pgs; English Abstract.

BaoFa Yu,"Interventional Oncology & Chemoimmunotherapy", Editor-in-Chief Baofa Yu, Military Medical Science Press, Sep. 30, 2014, p. 63-65.

Third office action of the Chinese counterpart applications.

COMPOSITION COMPRISING AN ALGAL PROTEOGLYCAN EXTRACT AND USE THEREOF

TECHNICAL FIELD

The present application relates to a composition comprising an algal extract and use thereof. In particular, the present application relates to a composition comprising an algal proteoglycan extract and use of the composition in treating or preventing tumor, pain, inflammation or diseases mediated by inflammatory factors.

BACKGROUND

Pancreatic cancer is a highly malignant gastro-intestinal (GI) cancer, which has a very poor prognosis. Both diagnosis and treatment of pancreatic cancer are difficult. Almost 90% of pancreatic cancer is ductal adenocarcinoma derived from glandular epithelium. In recent years, the morbidity and mortality of pancreatic cancer is increasing significantly with the five-year survival rate being <1%. It is one of the malignant tumors having the worst prognosis. Pancreatic cancer has low early diagnosis rate, high surgical mortality, and low cure rate. In recent years, the morbidity and mortality of other cancers are also increasing continuously.

The key to treatment of cancers, especially the pancreatic cancer, is to seek for an effective anti-tumor agent, which is also a focus of recent studies.

Since the 1970s, researchers have paid increasing attention to algae, especially blue-green algae. At first, the researchers mainly focused on the nutrition value and virulence of algae. In the meeting of the United Nations food and agriculture organization in 1974, spirulina was considered to be an excellent food resource for people in the future. Pharmaceutical uses of algae have been appreciated since the 1980s, and the research was mainly focused on the function of various algal extracts. The research on blue-green algae extract, especially the spirulina extract was particularly striking. The inventors in this application extracted an algal proteoglycan extract from the algae (see, the Chinese Patent CN1098707C). In the present application, the inventors studied the therapeutical effect of the algal proteoglycan extract on cancers (especially pancreatic cancer), as well as on pain (such as pain associated with tumors) and inflammation (such as inflammation associated with tumors).

SUMMARY OF THE INVENTIONS

In one aspect, the present application provides use of an algal proteoglycan extract or a composition comprising the algal proteoglycan extract in the manufacture of a medicament for treating or preventing pancreatic cancer in a subject. The pancreatic cancer is a primary cancer or a metastatic cancer.

The present application further provides use of an algal proteoglycan extract or a composition comprising the algal proteoglycan extract in the manufacture of a medicament for treating or preventing inflammation or pain. In certain embodiments, the above inflammation is tumor-associated inflammation, and the above pain is tumor-associated pain.

In another aspect, the present application provides a method for treating or preventing pancreatic cancer in a subject, which comprises administering a therapeutically or prophylactically effective amount of an algal proteoglycan extract or a composition comprising the algal proteoglycan extract to the subject. The present application further provides a method for treating or preventing inflammation or pain in a subject, which comprises administering a therapeutically or prophylactically effective amount of an algal proteoglycan extract or a composition comprising the algal proteoglycan extract to the subject.

In one aspect, the present application provides an algal proteoglycan extract or a pharmaceutical composition comprising the algal proteoglycan extract, for use in treating or preventing pancreatic cancer, pain or inflammation in a subject.

In certain embodiments, the algal proteoglycan extract and/or the extract together with one or more pharmaceutically acceptable carriers can be formulated into pharmaceutically acceptable dosage forms, preferably be formulated into oral liquids, tablets, granules, capsules, powders, pills, syrups and injections and the like.

In certain embodiments, the algal proteoglycan extract is administered orally, subcutaneously, intramuscularly or intraperitoneally. In a preferred embodiment, the algal proteoglycan extract is administered orally.

In certain embodiment, the dosage of the algal proteoglycan extract administrated to a subject is 5-500 mg/kg body weight per day. In a preferred embodiment, the dosage is 10-150 mg/kg body weight per day. In more preferred embodiments, the dosage is 20-120 mg/kg body weight per day.

In a further aspect, the present application provides use of an algal proteoglycan extract or a composition comprising the algal proteoglycan extract in the manufacture of a medicament for treating or preventing diseases mediated by inflammatory factors.

In a further aspect, the present application provides a pharmaceutical composition comprising an algal proteoglycan extract and one or more of other anti-tumor agents.

In some embodiments, the pharmaceutical composition comprising an algal proteoglycan extract and one or more of other anti-tumor agents is used to treat or prevent a tumor in a subject, wherein the tumor is preferably pancreatic cancer, melanoma or sarcoma. The algal proteoglycan extract and other anti-tumor agents have a synergistic effect on treatment of tumors and significantly improve the therapeutical efficacy on tumors.

In a further aspect, the present application further provides use of a pharmaceutical composition comprising an algal proteoglycan extract and one or more of other anti-tumor agents in the manufacture of a medicament for treating or preventing tumor in a subject.

In a further aspect, the present application further provides a method for treating or preventing a tumor in a subject, comprising administering a therapeutically or prophylactically effective amount of an algal proteoglycan extract or a pharmaceutical composition comprising the algal proteoglycan extract and one or more of other anti-tumor agents to the subject.

In certain embodiments, the tumor is a primary cancer or a metastatic tumor. In preferred embodiments, the tumor is selected from pancreatic cancer, melanoma, sarcoma, leukemia, lung cancer, esophagus cancer, lymphoma, stomach cancer, liver cancer, breast cancer, colon cancer, cutaneous squamous carcinoma or metastatic tumors thereof.

The present application further provides effects of an anti-tumor composition comprising the algal proteoglycan extract on anti-tumor immunity.

The above algal proteoglycan extract is prepared according to the method described in the Chinese Patent CN1098707C, which is incorporated herein by reference in its entirety. In particular, the method for preparing an algal proteoglycan extract comprises the following steps:

a. dissolving blue-green algae powder in 5-20 fold volume of water, and breaking cell wall;

b. heating the resulting mixture under 60-100° C., and performing solid-liquid separation after cooling;

c. adjusting the pH of the resulting liquid to less than 7, and performing solid-liquid separation again;

d. adjusting the resulting liquid to a neutral pH, concentrating, and drying if necessary.

The content of proteoglycan contained in the obtained algal proteoglycan extract is more than about 50% by weight, for example, more than about 60%, more than about 65%, more than about 70%, more than about 75%, and the like. In certain embodiments, the content of proteoglycan contained in the algal proteoglycan extract is about 70%-75% by weight.

DETAILED DESCRIPTION OF INVENTIONS

Figure 1:
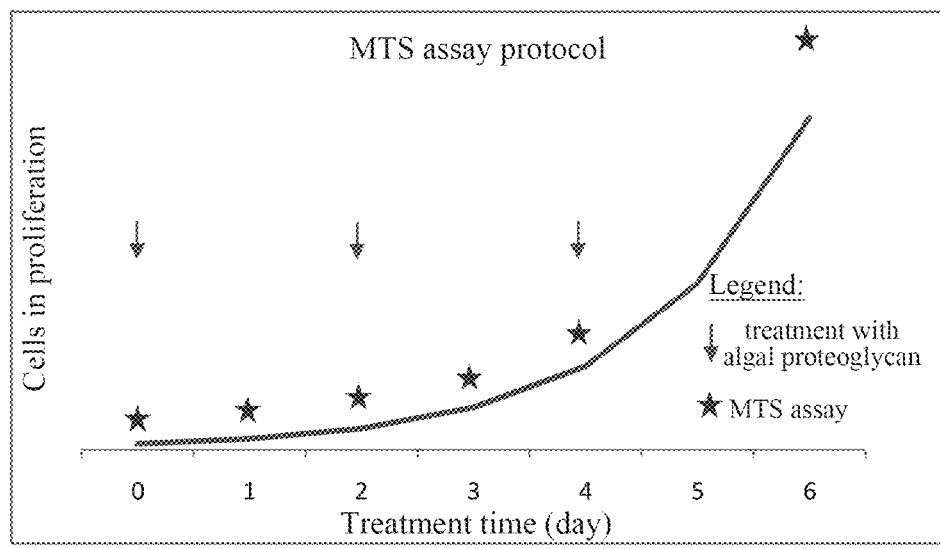
FIG. 1 shows the MTS assay protocol used for detecting the proliferation of PANC-1 cell line.

The present application provides use of an algal proteoglycan extract or a pharmaceutical composition comprising the algal proteoglycan extract in the manufacture of a medicament for treating or preventing a tumor such as pancreatic cancer, inflammation, pain, or diseases mediated by inflammatory factors.

The "pharmaceutically acceptable carrier" disclosed herein refers to a carrier which does not interfere with the bioactivity of active ingredients, including those commonly used in the pharmaceutical field. The pharmaceutically acceptable carrier disclosed herein can be solid or liquid, including pharmaceutically acceptable excipients, buffers, emulsifiers, stabilizers, preservatives, diluents, encapsulants, fillers and the like. For example, the pharmaceutically acceptable buffer further comprises phosphates, acetates, citrates, borates, carbonates and the like.

The pharmaceutical composition disclosed herein can be presented in the form of a unit dose, and can be prepared by any method well known in the pharmaceutical field. All of the methods comprise the step of combining the active ingredients disclosed herein with one or more pharmaceutically acceptable carriers. Generally, a composition is prepared by combining active ingredients with a liquid carrier or a solid carrier or both, followed by shaping the resultant product as required.

In certain embodiments, the algal proteoglycan extract disclosed herein and/or the extract together with a pharmaceutically acceptable carrier can be formulated into pharmaceutically acceptable dosage forms, for example, oral liquid, capsule, powder, tablet, granule, pill, syrup, injection, suppository and the like.

The algal proteoglycan extract disclosed herein is prepared according to the method described in the Chinese Patent CN1098707C, which is incorporated herein by reference in its entirety.

In certain embodiments, the algal proteoglycan extract disclosed herein is administered at a dosage of 5-500 mg/kg body weigh per day, preferably 20-150 mg/kg body weight per day, more preferably 20-120 mg/kg body weight per day, for example, 20 mg/kg body weight per day, 30 mg/kg body weight per day, 60 mg/kg body weight per day, 120 mg/kg body weight per day, and the like.

In another aspect, a method for treating or preventing tumors such as pancreatic cancer, inflammation, pain, or diseases mediated by inflammatory factors in a subject is provided, which comprises administering a therapeutically or prophylactically effective amount of an algal proteoglycan extract or a composition comprising the algal proteoglycan extract to the subject.

In a further aspect, use of a therapeutically or prophylactically effective amount of an algal proteoglycan extract or a composition comprising the algal proteoglycan extract in treating or preventing cancer, inflammation, pain or diseases mediated by inflammatory factors in a subject is provided.

The term "treating" or "treatment" used herein includes inhibiting, curing, relieving or alleviating cancer, pain (such as tumor-associated pain) or inflammation (such as tumor-associated inflammation) or diseases mediated by inflammatory factors, as well as preventing or delaying metastasis of a primary cancer.

In certain embodiments, the cancer can be a primary cancer, and can also be a metastatic cancer. In some embodiments, the cancer can be pancreatic cancer, liver cancer, colon cancer, gastric cancer, melanoma, sarcoma, leukemia, lung cancer, breast cancer, cutaneous squamous carcinoma, esophagus cancer, lymphoma and the like.

In some embodiments, the inflammatory factors disclosed herein include but not limited to histamine receptor H3, kallikrein-related peptidase 3, kallikrein-related peptidase 13, insulin-like growth factor 2, tumor necrosis factor, leukotriene B4 receptor 2, chemokine (C—C motif) ligand 4, colony stimulating factor 3 (granulocyte), dopamine receptor 4, platelet derived growth factor β polypeptide, kallikrein-related peptidase 11, kallikrein-related peptidase 15, leukotriene B4 receptor, leukotriene C4 synthase, chemokine (C—C motif) ligand 2, interleukin-6, interleukin-10, interferon-α receptor 2, platelet-derived growth factor A, platelet-derived growth factor C, platelet-derived growth factor D, C-reactive protein, kallikrein-related peptidase 14, bradykinin receptor B2, tumor necrosis factor (ligand) superfamily member 11, chemokine (C—C motif) ligand 3, chemokine (C—C motif) ligand 7, chemokine (C—C motif) ligand 20, chemokine (C—X—C motif) ligand 2, platelet derived growth factor β polypeptide, interferon (α, β and Ω) receptor 1, interleukin 3, interleukin 9, interleukin 17B, interleukin 20, growth differentiation factor 2, growth differentiation factor 3, macrophage migration inhibitory factor (glycosylation-inhibiting factor), grow differentiation factor 11, bone morphogenetic protein 2, bone morphogenetic protein 4, thrombopoietin, kallikrein-related peptidase 4, kallikrein-related peptidase 5, bradykinin receptor B1, interferon-α6, and the like.

In some embodiments, diseases or disorders mediated by inflammatory factors include but not limited to chronic bladder inflammation, urethritis, vestibular vertigo, anaphylaxis, asthma (bronchial asthma, childhood asthma), liver cancer (human hepatocellular carcinoma, primary liver cancer and the like), prostatic cancer, ovarian cancer, cervical cancer, breast cancer, testicular cancer, colorectal cancer, osteoarthritis, primary hypertension, myocardial infarction, myocardial infarction Parkinson's disease, Alzheimer disease, hereditary angioedema, hemangioma (infant), cardiovascular disease, colorectal cancer, purulent meningitis, endometrial cancer, spontaneous abortion, bladder cancer, glioma, liver fibrosis, cerebral hemorrhage, non-small cell lung cancer, acute myelocytic leukemia, cerebral infarction, pharyngeal tonsil hypertrophy, hepatitis C, multiple myeloma, systemic lupus erythematosus, pneumonia (bronchopneumonia, pediatric pneumonia, community-acquired pneumonia), ulcerative colitis, chronic obstructive pulmonary disease, pulmonary tuberculosis, Parkinson's disease, non-alcoholic fatty liver disease, hypertension (obesity-related hypertension, primary hypertension), autoimmune hepatitis, sclerosing cholangitis, normal-weight obesity syndrome, diabetic retinopathy, inflammatory bowel disease, hypersomnia, Behcet's disease, giant cell arteritis, squamous-cell carcinoma, basal cell carcinoma, muco-cutameous lymph node syndrome, colitis, allergic disease, pancreatic cancer, ovarian cancer, stomach cancer, stoke (cerebral apoplexy, ischemic stroke), drug-induced acute liver injury, chronic neutrophilic leukemia, schizophrenia, papillary thyroid carcinoma, meningiomas, diabetes mellitus (type 1 diabetes mellitus, type 2 diabetes mellitus), pulmonary thromboembolism, thyroiditis, multiple myeloma bone disease, chronic lymphocytic leukemia, chondrosarcoma, oral leukoplakia and squamous carcinomas, allergic rhinitis, chronic nasosinusitis, Listeria infection, myocarditis, multiple sclerosis, multiple myeloma, laryngocarcinoma, IgA nephropathy, viral myocarditis, colorectal cancer, psoriasis, discogenic lumbocrural pain, hepatitis B, lung cancer, pulpitis, hashimoto thyroiditis, papillary thyroid carcinoma, pulmonary tuberculosis, leukemia, kawasaki disease, aplastic anemia, polymyositis, Hodgkin's disease, myeloid leukemia, ankylosing spondylitis, chronic nasal-rhinosinusitis with nasal polyps, diffuse large B cell lymphoma, atopic dermatitis, chronic high altitude cor pulmonale, arthritis (osteoarthritis, rheumatoid arthritis, juvenile idiopathic arthritis, spondyloarthritis), non-small cell lung cancer, allergic rhinitis, lichen planus, unstable angina pectoris, acute coronary syndrome, periodontitis, coronary heart disease, atherosclerosis, teratocarcinoma, embryonal carcinoma, atopic dermatitis, endometrial cancer, acute pancreatitis, cervical squamous cell carcinoma, oral squamous cell carcinoma, nasopharyngeal carcinoma, esophageal squamous cell carcinoma, myelodysplastic syndrome, cerebral glioma, primary Sjogren's syndrome, anemia (aplastic anemia in children, aplastic anemia), cerebral palsy, neonatal hypoxie-ischemic encephalopathy, airway inflammation, obstructive sleep apnea hypo-pnea syndrome, gout, amygdalitis, acute respiratory distress syndrome, obsessive-compulsive disorder, non-alcoholic fatty liver disease, metabolic syndrome, neonatal sepsis, hand-foot-and-mouth disease, dermatomyositis, sepsis, encephalitis, eclampsia, cancer of biliary duct (hilar cholangiocarcinoma, diabetic macrovascular complication bile duct carcinoma), systemic sclerosis, colon cancer, polycystic ovarian syndrome, Netherton syndrome, celiac diseases, diabetic nephropathy and the like.

The "therapeutically effective amount" or "prophylactically effective amount" used herein can be determined as the case may be, and can be easily operated by a person having ordinary skills in the art according to the dosage actually required, for example, being determined according to the body weight, age and conditions of a patient. As all of the ingredients contained in the extract are nontoxic, the extract itself can be administered directly as required, where the composition does not comprise a pharmaceutically acceptable carrier. Where the composition comprises a pharmaceutically acceptable carrier, the extract and the carrier can be mixed by conventional methods in the pharmaceutical field to manufacture the required medicament.

In certain embodiments, the algal proteoglycan extract or a composition comprising the algal proteoglycan extract is administered orally, subcutaneously, intramuscularly or intraperitoneally. In preferred embodiments, the algal proteoglycan extract or a composition comprising the algal proteoglycan extract is administered orally.

The present application further provides a pharmaceutical composition comprising an algal proteoglycan extract and one or more of other anti-tumor agents.

The above anti-tumor agents includes those used clinically for treating tumors, for example, inhibitors of nucleotide synthesis (e.g. 5-fluorouracil (5-FU)); anti-tumor antibiotics (e.g. adriamycin (ADM)); platinum compounds (e.g. carboplatin); alkylating agents (e.g. cyclophosphamide and nitrosourea, such as carmustine); inhibitors of DNA polymerase (e.g. gemcitabine); agents interfering with protein synthesis (e.g. etoposide (VP-16)); and the like.

When the algal proteoglycan extract is administered in combination with one or more of other anti-tumor agents, the anti-tumor effect is enhanced significantly, exhibiting a synergistic effect. The synergistic effect of the combination therapy (e.g. the combination of the algal proteoglycan extract and one or more of other anti-tumor agents) allows lower dosage administrated to a subject suffering from a certain disorder (such as cancer or associated symptoms thereof) than that of each therapy alone, and/or reduced frequence of administration for the therapy.

The term "subject" used herein refers to a mammal, including but not limited to primates, bovine, horses, pigs, sheeps, goats, dogs, cats, and rodents such as rats and mice.

In the instant specification and claims, the terms "comprise/comprises/comprising", "include/includes/including" and "contain/contains/containing" mean "including but not limited to", and are not intended to exclude other parts, additives, components or steps.

It should be understood that the features, characteristics, components or steps described in the specific aspects, embodiments or examples in the present application can be applied to any other aspects, embodiments or examples described herein, unless indicated to the contrary.

The above disclosures describe the inventions in general, and the following examples further illustrate the inventions. These examples described are only intended to illustrate the inventions, but not considered as any limitation to the inventions. Although specific terms and values are used herein, these terms and values should also be interpreted to be illustrative, and do not limit the scope of the inventions. Unless indicated specifically, the experimental methods and techniques in the specification are methods and techniques well known to a person skilled in the art.

EXAMPLES

Example 1 Inhibitory Effect of Algal Proteoglycan Extract on Pancreatic Carcinoma Example 1.1 Algal Proteoglycan Extract Inhibited the Proliferation of PANC-1 Pancreatic Carcinoma Cells Cell Line & Cell Culture In this study, we used a pancreatic carcinoma cell line, PANC-1. This cell line is cultured by AnyGenes®. Several passages were conducted to ensure cell viability and allow the required amount of cells to perform different experiments (MTS tests and SignArrays® analysis). Information concerning the cell line PANC-1 was described in Table 1.

TABLE 1

| Cell line | Organism | Type | Characteristics | Origin |
|---|---|---|---|---|
| PANC-1 | *Homo Sapiens* | Pancreas | Epithelioid Carcinoma | ATCC ® RL-1469 ™ |

PANC-1 cells was grown in DMEM medium (Dulbecco's Modified Eagle's Medium; Gibco® by Life Technologies™) supplemented with 10% FBS (fetal bovine serum; Gibco® by Life Technologies™), 1% L-glutamine (200 mM; Gibco® by Life Technologies™), 1% Sodium Pyruvate (100 mM; Gibco® by Life Technologies™), 1% streptomycin-penicillin (10,000 U/mL Penicillin & 10,000 µg/mL Streptomycin; Gibco® by Life Technologies™) and incubated at 37° C. under 5% $CO_2$. Cell viability will be determined by Trypan blue exclusion assay.

Preparation of Algal Proteoglycan Extract 3 kg dried spirulina powder was rinsed with 3 liters of water, and filtered by suction. Then 30 liters of water was added to the resulting residue, and the mixture was stirred. The mixture was heated at 88° C. for 1 hour, cooled and then filtered under reduced pressure. The filtrate was adjusted with hydrochloric acid to pH 3.8, then put aside overnight for centrifugal separation. The supernatant was adjusted with $Na_2CO_3$ solution to pH 7, and then spray-dried to give 0.599 kg algae proteoglycan extract. The proteoglycan content in the extract was tested to be 72.3%.

The algae proteoglycan extract is weighed under sterile conditions and dissolved in 50 mg/ml PBS to give the stock solution. After centrifugation at 2,500 g for 30 minutes, the supernatant was filtered through a 0.2 µm filter. In a MTS assay, the solution was diluted in a medium to treat the cells. In the following parts, the algal proteoglycan extract is also referred to as "Extract K".

MTS Assay

The cell proliferation test was conducted by using the CellTiter 96® AQueous None Radioactive Cell Proliferation Assay (MTS; Promega), based on colorimetric method for determining the number of viable cells in proliferation.

This assay kit is composed of solutions of a tetrazolium salt (3-(4,5-dimethylthiazol-2-yl)-5-(3 carboxymethoxyphenyl)-2-(4-sulfophenyl)-2H-tetrazoliu m); MTS) and an electron coupling reagent (phenazine methosulfate; PMS) to increase the chemical stability of the compound. MTS is reduced by dehydrogenase enzymes found in metabolically active cells to a colored product soluble in culture medium: the formazan. The quantity of formazan product is measured after 2 hours of incubation at 37° C. by the amount of 490 nm absorbance, directly proportional to the number of living cells in culture. Finally, the half maximal inhibitory concentration (IC50) of the algal proteoglycan extract was determined with the experimental model PANC-1 cells. All the cell culture conditions are carried out in triplicate.

Cells were seeded on 96-well culture plates (Microtest 96®; Falcon) at Day −1 (D1) (1,500 cells per well in 100 µl medium), subsequently treated within the preselected concentration range. In particular, 10 different concentrations are selected for the algal proteoglycan extract, three wells for each concentration. Cell-free wells without addition of algal proteoglycan extract are used as control wells.

Just before adding MTS solution, cell culture medium with or without treatment was removed to avoid interference of the algae proteoglycan extract with this assay, and 100 µl medium was added to each well. Then, 20 µl of MTS solution was added in each well and measurement of the absorbance at 490 nm was performed after 4 hours of incubation at 37° C. under 5% $CO_2$. The cell culture medium with or without the algae proteoglycan extract was changed at days D2 (Day-2) and D4 (Day-4). OD values at 490 nm were measured at days D0, D1, D2, D3, D4 and D6, corresponding to the global analysis of 6×96-well plates (once per day), as illustrated in FIG. 1.

Results of the Cell Proliferation Assay on the PANC-1 Cell Line

MTS results at D0

OD values at D0 were measured for testing if the previous day's cell seeding is done in a proper way and if the adapted protocol is working on this cell line. Table 2 listed OD values at D0. We can observe that there was no significant statistical difference among the OD values, which indicated that the cell seeding was correct and the results were repeatable.

TABLE 2

| PANC-1 cell line | OD value | | | | | | Mean value | SD | Total mean value | Total SD |
|---|---|---|---|---|---|---|---|---|---|---|
| Day 0 | 0.507 | 0.476 | 0.499 | 0.491 | 0.497 | 0.494 | 0.494 | 0.01035 | 0.499 | 0.01063 |
|  | 0.496 | 0.495 | 0.508 | 0.493 | 0.487 | 0.5 | 0.497 | 0.00706 |  |  |
|  | 0.488 | 0.515 | 0.497 | 0.511 | 0.504 | 0.519 | 0.506 | 0.01169 |  |  |

Anti-Proliferative Effect of the Algae Proteoglycan Extract on PANC-1 Cell Line

OD values corresponding to different concentrations of the algae proteoglycan extract are presented in Table 3.

TABLE 3

| Extract K (mg/ml) | | 0 | 5 | 3.5 | 2.5 | 1.75 | 1 | 0.5 | 0.25 | 0.1 | 0.05 | 0.025 | cell-free control |
|---|---|---|---|---|---|---|---|---|---|---|---|---|---|
| Day 1 | OD value | 0.483 | 0.453 | 0.456 | 0.463 | 0.476 | 0.498 | 0.569 | 0.535 | 0.555 | 0.537 | 0.532 | 0.387 |
|  |  | 0.542 | 0.461 | 0.468 | 0.464 | 0.477 | 0.525 | 0.535 | 0.532 | 0.54 | 0.559 | 0.48 | 0.386 |
|  |  | 0.5 | 0.475 | 0.439 | 0.458 | 0.48 | 0.521 | 0.549 | 0.523 | 0.529 | 0.553 | 0.494 | 0.385 |
|  | mean value | 0.508 | 0.463 | 0.454 | 0.462 | 0.478 | 0.515 | 0.551 | 0.530 | 0.541 | 0.550 | 0.502 | 0.386 |
|  | SD | 0.030 | 0.0111 | 0.0146 | 0.0032 | 0.0021 | 0.0146 | 0.0171 | 0.0062 | 0.0131 | 0.0114 | 0.0269 | 0.0010 |

TABLE 3-continued

| Extract K (mg/ml) | | 0 | 5 | 3.5 | 2.5 | 1.75 | 1 | 0.5 | 0.25 | 0.1 | 0.05 | 0.025 | cell-free control |
|---|---|---|---|---|---|---|---|---|---|---|---|---|---|
| Day 2 | OD value | 0.653 | 0.41 | 0.463 | 0.451 | 0.474 | 0.592 | 0.522 | 0.59 | 0.518 | 0.557 | 0.642 | 0.382 |
| | | 0.691 | 0.42 | 0.506 | 0.441 | 0.433 | 0.61 | 0.499 | 0.611 | 0.533 | 0.605 | 0.597 | 0.382 |
| | | 0.656 | 0.416 | 0.439 | 0.462 | 0.515 | 0.608 | 0.598 | 0.554 | 0.557 | 0.58 | 0.479 | |
| | mean value | 0.667 | 0.415 | 0.469 | 0.451 | 0.474 | 0.603 | 0.540 | 0.585 | 0.536 | 0.581 | 0.573 | 0.382 |
| | SD | 0.021 | 0.0050 | 0.0340 | 0.0105 | 0.0410 | 0.0099 | 0.0518 | 0.0288 | 0.0197 | 0.0240 | 0.0842 | 0.0000 |
| Day 3 | OD value | 0.609 | 0.395 | 0.385 | 0.393 | 0.47 | 0.458 | 0.583 | 0.519 | 0.544 | 0.549 | 0.51 | 0.394 |
| | | 0.63 | 0.387 | 0.407 | 0.393 | 0.612 | 0.605 | 0.547 | 0.611 | 0.558 | 0.554 | 0.549 | 0.386 |
| | | 0.52 | 0.407 | 0.401 | 0.392 | 0.527 | 0.462 | 0.612 | 0.626 | 0.523 | 0.481 | 0.473 | 0.383 |
| | mean value | 0.586 | 0.396 | 0.398 | 0.393 | 0.536 | 0.508 | 0.581 | 0.585 | 0.542 | 0.528 | 0.511 | 0.388 |
| | SD | 0.058 | 0.0101 | 0.0114 | 0.0006 | 0.0715 | 0.0838 | 0.0326 | 0.0580 | 0.0176 | 0.0408 | 0.0380 | 0.0057 |
| Day 4 | OD value | 0.727 | 0.386 | 0.374 | 0.378 | 0.392 | 0.492 | 0.587 | 0.698 | 0.579 | 0.604 | 0.635 | 0.369 |
| | | 0.74 | 0.386 | 0.397 | 0.385 | 0.399 | 0.453 | 0.561 | 0.656 | 0.651 | 0.651 | 0.624 | 0.375 |
| | | 0.725 | 0.38 | 0.383 | 0.386 | 0.405 | 0.412 | 0.637 | 0.658 | 0.55 | 0.625 | 0.61 | 0.365 |
| | mean value | 0.731 | 0.384 | 0.385 | 0.383 | 0.399 | 0.452 | 0.595 | 0.671 | 0.593 | 0.627 | 0.623 | 0.370 |
| | SD | 0.008 | 0.0035 | 0.0116 | 0.0043 | 0.0065 | 0.0400 | 0.0386 | 0.0237 | 0.0520 | 0.0235 | 0.0125 | 0.0050 |
| Day 6 | OD value | 0.619 | 0.373 | 0.361 | 0.377 | 0.375 | 0.376 | 0.508 | 0.627 | 0.637 | 0.532 | 0.558 | 0.359 |
| | | 0.605 | 0.38 | 0.389 | 0.384 | 0.382 | 0.397 | 0.457 | 0.539 | 0.608 | 0.638 | 0.621 | 0.374 |
| | | 0.598 | 0.36 | 0.384 | 0.359 | 0.381 | 0.423 | 0.516 | 0.491 | 0.52 | 0.563 | 0.72 | 0.367 |
| | mean value | 0.607 | 0.371 | 0.378 | 0.373 | 0.379 | 0.399 | 0.494 | 0.552 | 0.588 | 0.578 | 0.633 | 0.367 |
| | SD | 0.010 | 0.0102 | 0.0149 | 0.0129 | 0.0038 | 0.0235 | 0.0320 | 0.0690 | 0.0609 | 0.0545 | 0.817 | 0.0075 |

Figure 2:
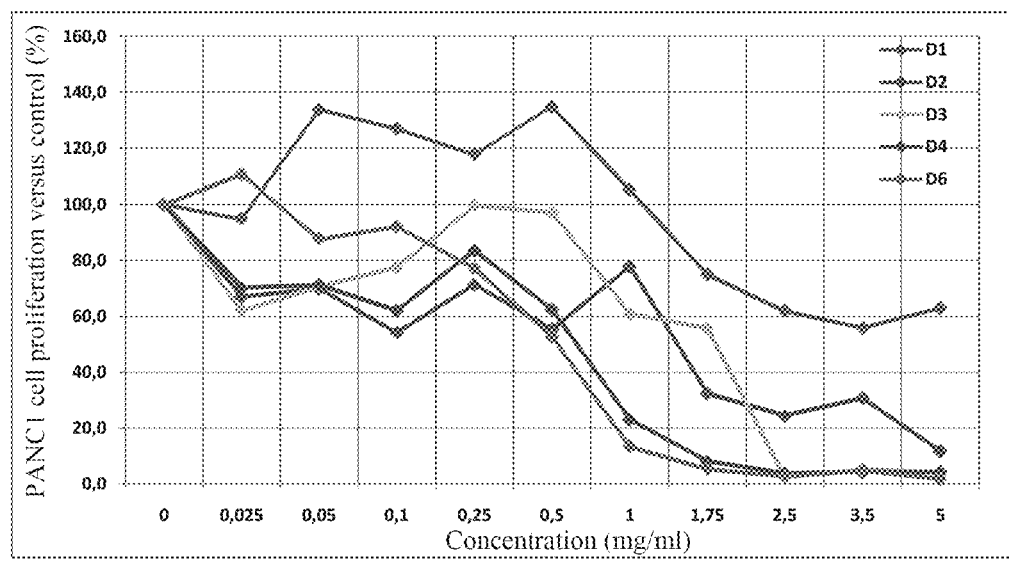
FIG. 2 shows the percentage of proliferation of PANC-1 cells after being treated with different concentrations of algal proteoglycan extract at day 1 (D1), day 2 (D2), day 3 (D3), day 4 (D4) and day 6 (D6), compared to the control.

Upon calculation, the percentage of cells in proliferation versus control (without Extract K) was determined. After treated with different concentrations of the algae proteoglycan extract each day, the percentage of cell proliferation of PANC-1 cell line versus control was presented in Table 4 and FIG. 2. Table 5 demonstrated the inhibition effect of the algae proteoglycan extract on PANC-1 cell proliferation. The inhibition percentage was calculated by comparing the survival cell number after treating with Extract K with the survival cell number without treatment.

inhibition for 5 mg/mL Extract K at D2 was 88.29%; and 1.75 mg/mL, 2.5 mg/mL, 3.5 mg/mL and 5 mg/mL Extract K all significantly inhibited the proliferation of PANC-1 cells with the percentage inhibition more than 90%.

The IC50 value of algae proteoglycan extract is >5 mg/ml at D1, and between 1 and 1.75 mg/ml at D2.

The above results showed that the algal proteoglycan extract disclosed herein has a remarkable inhibitory effect on PANC-1 pancreatic carcinoma cells.

TABLE 4

| Extract K | Percentage of cell proliferation versus control (%) | | | | | | | | | | |
|---|---|---|---|---|---|---|---|---|---|---|---|
| (mg/ml) | 0 | 0.025 | 0.05 | 0.1 | 0.25 | 0.5 | 1 | 1.75 | 2.5 | 3.5 | 5 |
| D1 | 100 | 94.82 | 133.79 | 126.98 | 117.71 | 134.88 | 105.18 | 74.93 | 61.85 | 55.86 | 62.94 |
| D2 | 100 | 66.98 | 69.79 | 54.10 | 71.31 | 55.39 | 77.75 | 32.32 | 24.36 | 30.68 | 11.71 |
| D3 | 100 | 61.91 | 70.64 | 77.52 | 99.50 | 97.15 | 60.74 | 55.79 | 2.52 | 5.03 | 4.36 |
| D4 | 100 | 70.18 | 71.19 | 61.96 | 83.38 | 62.42 | 22.90 | 8.03 | 3.69 | 4.16 | 3.97 |
| D6 | 100 | 110.66 | 87.67 | 92.11 | 77.15 | 52.77 | 13.30 | 5.26 | 2.77 | 4.71 | 1.80 |

TABLE 5

| Extract K | Percentage of inhibition of cell proliferation versus control (%) | | | | | | | | | | |
|---|---|---|---|---|---|---|---|---|---|---|---|
| (mg/ml) | 0 | 0.025 | 0.05 | 0.1 | 0.25 | 0.5 | 1 | 1.75 | 2.5 | 3.5 | 5 |
| D1 | 0 | 5.18 | −33.79 | −26.98 | −17.71 | −34.88 | −5.18 | 25.07 | 38.15 | 44.14 | 37.06 |
| D2 | 0 | 33.02 | 30.21 | 45.90 | 28.69 | 44.61 | 22.25 | 67.68 | 75.64 | 69.32 | 88.29 |
| D3 | 0 | 38.09 | 29.36 | 22.48 | 0.50 | 2.85 | 39.26 | 44.21 | 97.48 | 94.97 | 95.64 |
| D4 | 0 | 29.82 | 28.81 | 38.04 | 16.62 | 37.58 | 77.10 | 91.97 | 96.31 | 95.84 | 96.03 |
| D6 | 0 | −10.66 | 12.33 | 7.89 | 22.85 | 47.23 | 86.70 | 94.74 | 97.23 | 95.29 | 98.20 |

A significant anti-proliferative effect of the algae proteoglycan extract on PANC-1 cells was observed after treatment with 1.75 mg/mL, 2.5 mg/mL, 3.5 mg/mL or 5 mg/mL of Extract K at D1, D2, D3, D4 or D6. For example, the percentage inhibition for 2.5 mg/mL Extract K at D1 was 38.15% and the percentage inhibition for 5 mg/mL Extract K at D1 was 37.06%; the percentage inhibition for 2.5 mg/mL Extract K at D2 was 75.64%, and the percentage Example 1.2 Clinical Case of Algal Proteoglycan Extract for Treatment of Patients With Advanced Pancreatic Carcinoma Patient's condition: male, born in 1927, coronary stenting in 1996 for treatment of acute myocardial infarction; cardiac pacemaker implantation in 2003 for treatment of bradycardia; pancreatic head mass was found on Dec. 3, 2013 by ultrasound detection for treatment of febrile symptom; and poorly-differentiated advanced pancreatic carcinoma was diagnosed by percutaneous ultrasound-guided core-needle biopsy of pancreatic head mass on Dec. 26, 2013. On Jan. 14, 2014, PTCD+biliary stenting were performed. The algal proteoglycan extract prepared according to Example 1.1 was administrated to the patient on Dec. 15, 2013, 1,350 mg/d, increased to 2,025 mg/d after 20 days. The patient received no other treatment.

Clinical efficacy observation: the patient's condition was stabilized after partial remission (PR), and the overall survival was 20 months.

Figure 3:
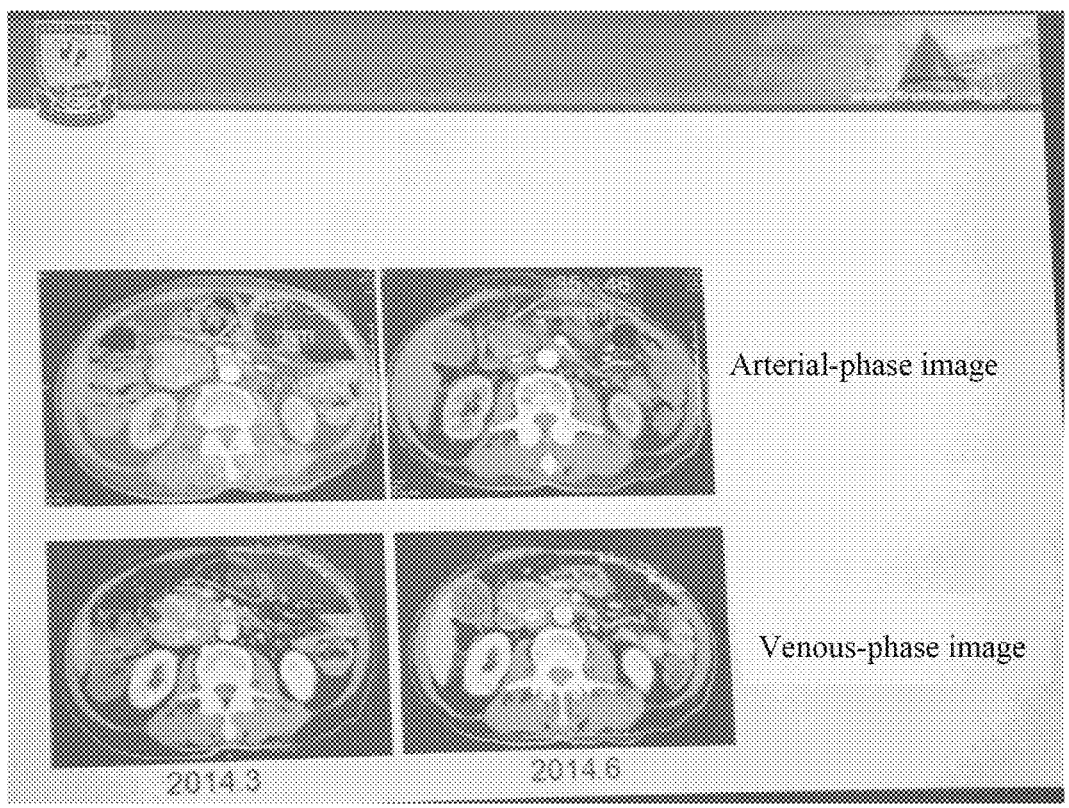
FIG. 3 shows CT imaging changes of the pancreas in a patient with advanced pancreatic cancer after taking the algal proteoglycan extract for 3 months.

FIG. 3 showed CT imaging changes in the pancreas of the patient after administration of the algal proteoglycan extract for three months. The arterial-phase image showed that the tumor shrank from 46×51 mm to 35×46 mm after 3 months. The venous-phase imaging showed that the density of the central necrotic area was significantly reduced. This further confirmed that the algal proteoglycan extract disclosed herein can be used for treatment of pancreatic carcinoma, and has a significant inhibitory effect on advanced pancreatic carcinoma.

Pancreatic carcinoma is a highly malignant digestive tract cancer. The patients with pancreatic carcinoma will have a survival of about 4 months without any treatment, or 16 months after resection. However, due to low diagnosis rate of early pancreatic carcinoma, most cases have developed to the advanced stage when diagnosed, which is not suitable for surgical treatment. The existing drug therapies cannot effectively prolong the survival of patients. The inventors summarized the effects of drug therapies reported in the prior art literature (Table 6). It can be seen from Table 6 that even with combination therapy, the overall survival was at most 9 months. Surprisingly, the patient with advanced pancreatic carcinoma in this Example, after taking the algal proteoglycan extract, obtained an unexpected 20-month overall survival. This demonstrates that the algal proteoglycan extract disclosed herein is significantly superior to the existing drug therapies in the treatment of pancreatic carcinoma patients, and this effect is unexpected.

TABLE 6

| Researcher | Number of cases | Experimental scheme | Overall survival |
|---|---|---|---|
| Berlin et al | 322 | Gemcitabine vs. Gemcitabine + 5-FU | 5.4 vs. 6.7 months (p = 0.09) |
| Rocha Lima et al | 342 | Gemcitabine vs. Gemcitabine + irinotecan | 6.3 vs. 6.6 months (p = 0.79) |
| Louvet et al | 313 | Gemcitabine vs. Gemcitabine + oxaliplatin | 7.1 vs. 9.0 months (p = 0.13) |
| Oettle et al | 565 | Gemcitabine vs. Gemcitabine + irinotecan | 6.3 vs. 6.2 months (p = 0.79) |
| Heinemann et al | 195 | Gemcitabine vs. Gemcitabine + cisplatin | 6.0 vs. 7.5 months (p = 0.15) |
| Starhopoulos et al | 145 | Gemcitabine vs. Gemcitabine + irinotecan | 6.4 vs. 6.5 months (p = 0.97) |
| Abou-Alfa et al | 349 | Gemcitabine vs. Gemcitabine + exatecan | 6.2 vs. 6.7 months (p = 0.52) |
| Hermann et al | 319 | Gemcitabine vs. Gemcitabine + capecitabine | 7.2 vs. 8.4 months (p = 0.234) |
| Cunningham et al | 533 | Gemcitabine vs. Gemcitabine + capecitabine | 7.1 vs. 6.2 months (p = 0.08) |
| Poplon et al | 832 | Gemcitabine vs. Gemcitabine FDR. Vs Gemcitabine + oxaliplatin | 4.9 vs. 6.2 months (p = 0.04) vs 5.7 months (p = 0.22) |
| Colucci et al | 400 | Gemcitabine vs. Gemcitabine + eisplatin | 7.2 vs. 8.2 months (p = 0.38) |

Example 2 Therapeutic Effect of the Algal Proteoglycan Extract on Liver Cancer

In this example, the effect of the algal proteoglycan extract on the median survival time of 11 patients with hepatocellular carcinoma was examined.

Eleven patients with hepatocellular carcinoma were treated with the algal proteoglycan extract prepared according to Example 1.1 (1,080 mg/d), until the patient was dead or oral administration became impractical. The survival times of all the cases were 2~43 months, and the median survival time was 15.2 months for 11 patients with HCC. The longest survival time was 43 months, 4 patients gained a survival time of more than 20 months, 8 patients gained a survival time of more than 11 months, 9 patients gained a survival time of more than 6 months, and 1 patient gained a survival time of less than 3 months. In these cases, a special patient recommended by Anhui Charity Federation, ZBFU from Anhui Hospital, was diagnosed with primary liver cancer on Aug. 2, 2005, T2N0M0, stage II, with space occupying lesion of 3.0*3.7 cm in the right lobe of liver; and due to splenomegaly, liver cirrhosis, left kidney stone accompanied by bleeding, no other treatment was given. This patient entered the study on Sep. 24, 2005 and began to take the algal proteoglycan extract prepared in accordance with Example 1.1. ZBFU died on Apr. 6, 2009. This patient took the algal proteoglycan extract continuously and survived for 43 months.

The survival time of patients with liver cancer has been the most difficult problem in the treatment of liver cancer. Various chemotherapies for inoperable patients can only prolong the median survival time by 1-2 months. Currently, the standard medication for liver cancer is Sorafenib (trade name: NEXAVAR), with a median survival time of 10.7 months and 7.9 months in the treatment group and placebo control group, respectively. However, in this Example, after taking the algal proteoglycan extract, the patients with liver cancer have a median survival time of 15.2 months. This demonstrates that the algal proteoglycan extract disclosed herein is significantly superior to the existing medicament in treating liver cancer.

Example 3 Therapeutic Effect of Algal Proteoglycan Extract on Colon Cancer

In this example, the therapeutic effect of the algal proteoglycan extract on eight patients with colon cancer was examined.

Among these 8 patients with colon cancer, 2 patients are males and 6 patients are females, aged 38 to 68, and the median age is 60.5; and the physical condition rating ranged from 70 to 90. Two patients suffered from clinical stage III colon cancer, and six patients suffered from clinical stage IV colon cancer; and thus all cases were clinical stage III or IV tumors. 8 cases were pathologically diagnosed (8 cases receiving surgery).

| General condition of subjects with colon cancer | | | |
|---|---|---|---|
| Gender | Male | 2 cases | 25.00% |
| | Female | 6 cases | 75.00% |
| Age(year) | Range | 38-68 | |
| | Median age | 60.5 | |
| | >65 | 2 cases | 25.00% |
| | ≤65 | 6 cases | 75.00% |
| Physical | >80 | 4 cases | 50.00% |
| condition rating | 70-80 | 4 cases | 50.00% |
| | Median KPS | 85 | |
| Diagnosis method | Pathology | 8 cases | 100.00% |
| History of prior | Surgery + chemotherapy | 3 cases | 37.50% |
| treatment | Surgery + radiotherapy + chemotherapy | 5 cases | 62.50% |
| Recurrence & | Relapse | 2 cases | 25.00% |
| metastasis | Distant metastasis | 6 cases | 75.00% |
| Stage | IIIA/IIIB | 2 cases | 25.00% |
| | IV | 6 cases | 75.00% |

Eight patients with colonic cancer took the algal proteoglycan extract prepared according to Example 1.1 at a dosage of 1,080 mg/d. After 56 days of treatment, 1 case showed partial remission (PR), 3 cases showed stabilized disease (SD), 4 cases showed progressive disease (PD). The efficacious rate (CR+PR/total number of cases) for treatment of the eight colon cancer cases was 12.5%, and the disease control rate (CR+PR+SD/total number of cases) was 50%.

Example 4 Therapeutic Effect of the Algal Proteoglycan Extract on Gastric Cancer The therapeutic effect of algal proteoglycan extract on patients with gastric cancer was also studied.

Among three patients with gastric cancer, all were male, aged 57 to 67, with a median age of 65. Three patients were all in advanced stage, in which 2 cases were clinical stage III tumors, and 1 case was clinical stage IV tumor; and the tissue type of all cases was adenocarcinoma. Three cases were pathologically diagnosed (including 1 case receiving biopsy and 2 cases receiving surgery).

Three patients with gastric cancer took the algal proteoglycan extract prepared according to Example 1.1 at a dosage of 1,080 mg/d. After 56 days of treatment, 2 cases showed stabilized disease (SD), 1 case showed progressive disease (PD), and the disease control rate was 66.7%.

Example 5 Therapeutic Effect of the Algal Proteoglycan Extract on Lymphoma

In this example, the therapeutic effect of the algal proteoglycan extract on the patients with lymphoma was examined.

Patient's condition: 62-year-old female, diagnosed as non-Hodgkin's lymphoma NHL (diffuse large B), stage IVB (end-stage tumor). The prior treatment included 6 courses of CHOP chemotherapy, 8 courses of IMVP-16 chemotherapy, and 2 courses of HDAra-c+VP-16 chemotherapy. After the above treatment, a 3×2 cm mass was found in the left submandibular region.

Since Mar. 2, 2003, the patients with non-Hodgkin's diffuse large B lymphoma who had relapsed after multiple chemotherapies began taking the algae proteoglycan extracts prepared according to Example 1.1 orally at a dosage of 2,700 mg/d, three times a day. On Mar. 31, 2003, the lesion size was reduced to 1.5×1.8 cm. The clinical efficacy was evaluated as partial remission (PR).

The above patient with recurrent non-Hodgkin's diffuse large B lymphoma after multiple chemotherapies achieved partial remission after 28 days of treatment with the algal proteoglycan extract, which demonstrates that the algal proteoglycan extract disclosed herein has a significant therapeutic effect on lymphoma.

Example 6 Therapeutic Effect of the Algal Proteoglycan Extract on Esophageal Cancer In this example, the therapeutic effect of the algal proteoglycan extract on patients with esophageal cancer was examined.

Two patients with esophageal cancer were enrolled in the study with the physical condition rating of 80, and both were in advanced stage (stage III and stage IV), with distant metastases. After treatment with the algal proteoglycan extract prepared in accordance with example 1.1, one case showed partial remission (PR), and one case showed stabilized disease (SD), as shown in the table below.

| Tumor Evaluation of Assessable Patients with Esophageal Cancer | | | | |
|---|---|---|---|---|
| No. | Abbreviated name | Serial No. | Tumor stage | Tissue type | Therapeutic effect |
| 1 | SXFA | 3 | IV | Adenocarcinoma | SD |
| 2 | ZSCA | 2 | IV | Squamous cell carcinoma | PR |

Next, the specific conditions of the two patients were described.

Patient SXFA, male, born on Mar. 19, 1941, his condition and treatment were as follows:

The patient was diagnosed by tissue biopsy with poorly differentiated adenocarcinoma of esophagus, stage IV, on Nov. 10, 2005.

On Nov. 8, 2005, the CT imaging result showed a 6 cm-long nodular uplift in the mucosa located at 40 mm from the incisors line with hemorrhagic erosions.

From Aug. 13, 2006 to Nov. 15, 2006, the patient took orally the algal proteoglycan extract prepared according to Example 1.1 at a dose of 1,080 mg/d continuously, without receiving any other treatment before and during administration of the algal proteoglycan extract.

On Oct. 13, 2006, the CT imaging result showed 5 cm irregular filling defect in lower esophagus, and the lesion height was 5 mm.

The therapeutic efficacy was evaluated as stabilized disease (SD).

Patient ZSCA, male, born on Jul. 17, 1957, his condition and treatment were as follows:

The patient was diagnosed by the puncture and smear with esophageal squamous cell carcinoma by the puncture and smear, stage IV, on May 15, 2006.

On May 17, 2006, the CT imaging result showed 5.5×5 cm lymph node in the right clavicle.

From May 17, 2006 to Nov. 1, 2006, the patient took orally the algal proteoglycan extract prepared according to Example 1.1 at a dose of 1,080 mg/d continuously, without receiving any other treatment before and during administration of the algal proteoglycan extract.

On Nov. 1, 2006, the CT imaging result showed 2.5×2 cm lymph node in the right clavicle.

The therapeutic efficacy was evaluated as s partial remission (PR).

The above data show that the algal proteoglycan extract disclosed herein has also a therapeutic effect on esophageal cancers.

Example 7 Algal Proteoglycan Extract Alleviated Tumor-Associated Pain

Example 7.1 Therapeutic Effect of the Algal Proteoglycan Extract on Liver Cancer Pain Pain is a common clinical symptom of advanced liver cancer, and seriously affects patients' life quality. Strong analgesic drugs were conventionally used to control the pain. In this Example, 18 patients with hepatocellular carcinoma were chosen for studying the inhibitory or prophylactic effect of the algal proteoglycan extract on pain.

Eighteen patients with hepatocellular carcinoma were treated with the algal proteoglycan extract prepared in accordance with Example 1.1 at a dose of 1,080 mg/d, until the patients were dead or oral administration became impractical. All cases did not take other analgesic drugs during the study, and 14 patients' pain was measured by a pain scale. Among these 14 cases, 2 cases showed no pain throughout; 7 cases showed pain relief; 5 cases maintained mild pain of 1-2 degree, without change. Typical cases included the following patients.

One patient needed to take strong morphine analgesic drugs when entering the study, and the analgesic drugs were not needed shortly after administration of the algae proteoglycan extract. Another patient had a huge tumor (8×8.5 cm) detected by imaging examination, but no pain symptom appeared in the patient after administration of the algae proteoglycan extract.

The above data showed that the algal proteoglycan extract disclosed herein has a significant inhibitory and ameliorating effect on pain.

Pain assessment scales used herein are as follows:

---

Rating of the Patients' Life Quality

A. Appetite:
①. Food intake almost impossible;
②. Food intake < ½ of normal intake;
③. Food intake = ½ of normal intake;
④. Food intake slightly reduced;
⑤. Food intake remains normal.

B. Sleep:
①. Difficult to fall asleep;
②. Very poor sleep;
③. Poor sleep;
④. Slightly poor sleep;
⑤. Roughly normal.

C. Pain:
①. Severe pain, with passive position, intolerable;
②. Severe pain;
③. Moderate pain;
④. Mild pain;
⑤. Painless.

D. Tumor-related symptoms (except for pain):
①. Severe, intolerable;
②. Severe;
③. Moderate;
④. Mild;
⑤. No.

E. PS (ECOG):
①. IV; ②. III; ③. II; ④. I; ⑤. 0.

---

Example 7.2 Therapeutic Effect of the Algal Proteoglycan Extract on Pancreatic Carcinoma Pain The inhibitory effect of the algal proteoglycan extract on pain in 24 patients with pancreatic cancer and pain symptoms were also studied. 24 patients with pancreatic carcinoma enrolled in the study were treated with the algal proteoglycan extract prepared in accordance with Example 1.1 at a dose of 2,025 mg/d, until the patients were dead or oral administration became impractical. The pain symptoms in 24 patients were significantly alleviated, as measured by pain assessment scale.

Example 8 Inhibition Effect of the Algal Proteoglycan Extract on Inflammation Tumor-promoting inflammation is considered to be one of the characteristics of cancer. Chronic inflammatory diseases can increase the risk of certain cancers and a number of epidemiological evidence suggests that NSAIDs, especially aspirin, are potent chemical prophylaxis agents. There are many different inflammatory cells in the tumor microenvironment; and targeting these factors in hereditary, transplantable and inducible mouse models of cancer can significantly reduce the onset, development and spread of tumor diseases. Therefore, this complex network of inflammation provides a target for malignant disease prevention and treatment. This Example examined the effect of the algal proteoglycan extract on the expression of inflammatory mediators in cancer cells.

Example 8.1 Regulatory Effect of the Algal Proteoglycan Extract on Inflammatory Mediators Expression in Pancreatic Cancer Model According to the protocols described in Example 1, the algal proteoglycan extract was prepared and the PANC-I pancreatic carcinoma cell line was cultured.

The cells were seeded on 100 mm petri dishes (Corning®) (250,000 cells per petri dish in 16 ml medium) at Day 1. PANC-1 cells were treated with 5 mg/ml algae proteoglycan extract or PBS-containing medium (control) at Day 2. Cells were divided into three groups: the control group, the 3-hour treatment group and the 18-hour treatment group, each group being repeated twice.

By using the SignArrays® system by AnyGenes®, the expression of factors associated with six qPCR signaling pathways (SignArrays® by AnyGenes®) including angiogenesis, inflammation, interferon & immune system, cytokines, oxidative stress, and HLA systems was studied. Table 7 listed the number of factors whose expression was significantly down-regulated (at least 1-fold or more) compared to the control sample, among 76 inflammatory mediators examined. The fold change of some exemplary factors which were down-regulated compared to the control was listed in Table 8.

TABLE 7

| Treatment time | Number of factors with significantly down-regulated expression | Number of factors down-regulated 2-fold or more |
|---|---|---|
| 3 hours | 46 | 12 |
| 18 hours | 55 | 13 |

TABLE 8

| Name of factors | Symbols | Fold change (3-hr or 18-hr treatment) |
|---|---|---|
| Histamine receptor H3 | HRH3 | 3.46 |
| kallikrein-related peptidase 3 | KLK3 | 3.07 |
| kallikrein-related peptidase 13 | KLK13 | 3.07 |
| Insulin-like growth factor 2 | IGF2 | 3.66 |
| Tumor necrosis factor | TNF | 2.8 |
| Leukotriene B4 receptor 2 | LTB4R2 | 2.62 |
| Chemokine (C-C motif) ligand 4 | CCL4 | 2.48 |
| Colony stimulating factor 3 (granulocyte) | CSF3 | 2.79 |
| Dopamine receptor 4 | DRD4 | 4.13 |
| Platelet-derived growth factor beta polypeptide | PDGFB | 2.49 |
| kallikrein-related peptidase 11 | KLK11 | 3.22 |
| kallikrein-related peptidase 15 | KLK15 | 1.15 |
| Leukotriene B4 receptor | LTB4R | 2.04 |
| Leukotriene C4 synthase | LTC4S | 2.38 |
| Chemokine (C-C motif) ligand 2 | CCL2 | 1.39 |
| Interleukin 6 | IL6 | 1.41 |
| Interleukin 10 | IL10 | 1.46 |
| Interferon (α) receptor 2 | IFNAR2 | 1.08 |
| Platelet-derived growth factor A | PDGFA | 1.15 |
| Platelet-derived growth factor C | PDGFC | 1.2 |
| Platelet-derived growth factor D | PDGFD | 1.97 |
| C-reactive protein | CRP | 1.93 |

From the above results, it can be seen that the algal proteoglycan extract disclosed herein can regulate the expression of various inflammatory mediators and cytokines in PANC-1 pancreatic carcinoma cells, and has a significant inhibitory effect on the expression of multiple inflammatory factors.

Example 8.2 Regulatory Effect of the Algal Proteoglycan Extract on Expression of Inflammatory Mediators in Liver Cancer and Lung Cancer Models In the present study, HuH7 hepatocellular carcinoma cell lines and A549 lung adenocarcinoma cell lines were used. The two cell lines were cultured by AnyGenes®.

HuH7 cells were grown in DMEM medium supplemented with 10% FBS (fetal bovine serum, Gibco® by Life Technologies™), 1% L-glutamine (200 mM; Gibco® by Life Technologies™), 1% sodium pyruvate (100 mM; Gibco® by Life Technologies™) and 1% streptomycin-penicillin (10,000 U/mL penicillin & 10,000 µg/mL streptomycin; Gibco® by Life Technologies™), and incubated in 37° C. under 5% CO2. Cell viability was determined by trypan blue exclusion assay.

A549 cells were grown in RPMI medium supplemented with 10% FBS (fetal bovine serum; Gibco® by Life Technologies™), 1% L-glutamine (200 mM; Gibco® by Life Technologies™), 1% sodium pyruvate (100 mM; Gibco® by Life Technologies™), 1% streptomycin-penicillin (10,000 U/mL Penicillin & 10,000 µg/mL Streptomycin; Gibco® by Life Technologies™), and incubated in 37° C. under 5% CO2. Cell viability was determined by trypan blue exclusion assay.

The algal proteoglycan extract was prepared according to the protocol described in Example 1. The expression of the relevant factors was examined according to the method described in Example 3.1. Table 9 listed the number of inflammatory mediators and cytokines examined in A549 cells and in HuH7 cells, and the number of factors whose expression was significantly down-regulated (at least 2-fold or more) compared to the control samples after 6 or 12 hours of treatment. Table 10 showed the fold change of some exemplary factors which were down-regulated compared to the control.

TABLE 9

|  | Number of tested factors | Number of factors down-regulated 2-fold or more |
|---|---|---|
| A549 cell | 63 | 54 |
| HuH7 cell | 29 | 28 |

TABLE 10

| Name of factors | Symbols | Fold change (in A549 cells) | Fold change (in HuH7 cells) |
|---|---|---|---|
| kallikrein-related peptidase 11 | KLK11 | 11.70 |  |
| kallikrein-related peptidase 14 | KLK14 | 7.27 |  |
| Bradykinin receptor B2 | BDKRB2 | 9.73 |  |
| Tumor necrosis factor | TNF | 18.69 |  |
| Tumor necrosis factor (ligand) superfamily member 11 | TNFSF11 |  | 5.07 |
| Chemokine (C-C motif) ligand 3 | CCL3 | 8.25 | 8 |
| Chemokine (C-C motif) ligand 7 | CCL7 | 11.64 | 12.51 |
| Chemokine (C-C motif) ligand 20 | CCL20 | 6.27 | 4.71 |
| Chemokine (C-X-C motif) Ligand 2 | CXCL2 |  | 13.77 |
| Platelet-derived growth factor beta polypeptide | PDGFB | 2.75 |  |
| Interferon (α, β and Ω) receptor 1 | IFNAR1 | 5.01 |  |
| Interleukin 3 | IL3 | 10.5 |  |
| Interleukin 9 | IL9 |  | 13.88 |
| Interleukin 17B | IL17B |  | 15.21 |
| Interleukin 20 | IL20 |  | 45.27 |
| Growth differentiation factor 3 | GDF3 | 36.53 |  |
| Macrophage migration inhibitory factor (glycosylation-inhibitory factor) | MIF | 5.89 |  |
| Growth differentiation Factor 2 | GDF2 |  | 1172.65 |
| Growth differentiation factor 11 | GDF11 |  | 8.42 |
| Bone morphogenetic protein 2 | BMP2 | 5.67 | 2.72 |
| Bone morphogenetic protein 4 | BMP4 | 2.36 | 6.04 |
| Thrombopoietin | THPO |  | 6.29 |
| kallikrein-related peptidase 4 | KLK4 |  | 4.48 |
| kallikrein-related peptidase 5 | KLK5 |  | 6.92 |
| Platelet-derived growth factor C | PDGFC | 2.83 | 2.52 |
| Platelet-derived growth factor D | PDGFD | 3.15 |  |
| kallikrein-related peptidase 15 | KLK15 | 2.32 |  |
| C-reactive protein | CRP | 25.15 | 12.15 |
| Bradykinin receptor B1 | BDKRB1 | 2.71 |  |
| Interleukin α6 | IFNA6 | 27.34 |  |

The results in Examples 8.1 and 8.2 show that the algal proteoglycan extract disclosed herein appears to be a major modulator for regulating expression of inflammatory mediators and cytokines in a variety of cancer models and can significantly inhibit expression of various proinflammatory cytokines, which demonstrates that the algal proteoglycan extract disclosed herein is capable of inhibiting the occurrence and progression of inflammation, in particular tumor-associated inflammation.

In addition, Table 11 below shows the corresponding relationship between inflammatory factors and diseases mediated by the factors, from which it can be seen that the inflammatory mediators and cytokines that are regulated by the algal proteoglycan extract disclosed herein can mediate the development of various diseases. Therefore, the algae proteoglycan extracts capable of down-regulating these inflammatory factors can be used to treat or prevent a variety of diseases and disorders associated with the inflammatory factors, including but not limited to the diseases or disorders listed in table 11.

TABLE 11

| Name of Factors | Corresponding Diseases |
| --- | --- |
| Histamine receptor H3 (HRH3) | chronic bladder inflammation, urethritis, vestibular vertigo, anaphylaxis, asthma, liver cancer, colon cancer |
| kallikrein-related peptidase 3 (KLK3) | Prostate cancer, colorectal cancer, testicular cancer |
| kallikrein-related peptidase 11 (KLK11) | Prostate cancer, gastric cancer |
| kallikrein-related peptidase 14 (KLK14) | colorectal cancer, ovarian cancer, cervical cancer, |
| Insulin-like growth factor 2 (IGF2) | Hemangioma (infant), cardiovascular disease, colorectal cancer, purulent meningitis, endometrial cancer, human hepatocellular carcinoma, primary liver cancer, spontaneous abortion, bladder cancer, schizophrenia, brain glioma, liver cancer, gastric cancer, liver fibrosis, colorectal cancer, cerebral hemorrhage, non-small cell lung cancer, hepatitis B, breast cancer, acute myeloid leukemia |
| Tumor necrosis factor (TNF) | cerebral infarction, pharyngeal tonsil hypertrophy, hepatitis C, multiple myeloma, systemic lupus erythematosus, rheumatoid arthritis inflammation, mycoplasma pneumonia, ulcerative colitis, bronchial asthma, chronic obstructive pulmonary disease, tuberculosis, Parkinson's disease, non-alcoholic fatty liver disease, obesity-type hypertension, juvenile idiopathic arthritis, allergic rhinitis, pancreatic cancer, non-small cell lung cancer, gastric cancer, hepatocellular carcinoma, coronary heart disease, autoimmune hepatitis, sclerosing cholangitis, breast cancer, normal-weight obesity syndrome, diabetic retinopathy, hepatitis C, psoriasis, cervical cancer, spondyloarthritis, inflammatory bowel disease, lupus erythematosus, hypersomnia, lung cancer, Behcet's disease, giant cell arteritis |
| Leukotriene B4 receptor 2 (LTB4R2) | Non-small cell lung cancer, squamous cell carcinoma, basal cell carcinoma, psoriasis vulgaris, muco-cuta-meous lymph node syndrome, colitis, rheumatoid arthritis, juvenile idiopathic arthritis, allergic disease, airway inflammation, pancreas cancer, leukemia, ovarian cancer, allergic disease, bronchial asthma, gastric cancer, ischemic stroke |
| Chemokine (C-C motif) ligand 4 (CCL4) | drug-induced acute liver injury |
| Colony stimulating factor 3 (granulocyte)(CSF3) | Chronic neutrophilic leukemia, systemic lupus erythematosus |
| Dopamine receptor 4 (DRD4) | Schizophrenia |
| Platelet-derived growth factor beta polypeptide (PDGFB) | Papillary thyroid carcinoma, bronchial asthma, meningioma, type-2 diabetes, pulmonary thromboembolism |
| Bradykinin receptor B2 (BDKRB2) | Osteoarthritis, hypertension, myocardial infarction, Parkinson's disease, osteoarthritis, Alzheimer's disease, hereditary angioedema |
| Tumor necrosis factor (ligand) superfamily member 11 (TNFSF11) | Thyroiditis, papillary thyroid carcinoma |
| Chemokine (C-C motif) ligand 3 (CCL3) | Chronic hepatitis B, tuberculosis, multiple myeloma bone disease, chronic lymphocytic leukemia, systemic lupus erythematosus, chondrosarcoma |
| Chemokine (C-C motif) ligand 7 (CCL7) | Oral leukoplakia and squamous cell carcinoma, allergic rhinitis, chronic sinusitis, Listeria infection, ulcerative colitis, myocarditis and multiple sclerosis, multiple myeloma, gastric cancer, chronic hepatitis B, prostate cancer, laryngeal cancer |
| Chemokine (C-C motif) ligand 20 (CCL20) | IgA nephropathy, liver cancer, viral myocarditis, chronic obstructive pulmonary disease, colorectal cancer, psoriasis, gastric cancer, laryngeal squamous cell carcinoma, discogenic lumbocrural pain, chronic hepatitis B, systemic lupus erythematosus, lung cancer, breast cancer, brain stroke, colon cancer, pulpitis, non-small cell lung cancer, esophageal squamous cell carcinoma |
| Chemokine (C-X-C motif) Ligand 2 (CXCL2) | Prostate cancer, colorectal cancer, Hashimoto's thyroiditis, papillary thyroid carcinoma, tuberculosis |
| Interleukin 3 (IL3) | Leukemia, colorectal cancer, Kawasaki disease, aplastic anemia, liver cancer |
| Interferon (α, β and Ω) receptor 1 (IFNAR1) | Chronic hepatitis B, chronic hepatitis C, gastric cancer, systemic lupus erythematosus, polymyositis, polydermatomyositis |
| Interleukin 9 (IL9) | Hodgkin's disease, myeloid leukemia, hepatitis B, ankylosing spondylitis, chronic nasal-rhinosinusitis with nasal polyps, diffuse large B-cell lymphoma, atopic dermatitis, chronic high altitude cor pulmonale, lupus erythematosus, arthritis, rheumatoid disease, bronchial asthma, chronic obstructive pulmonary disease |

TABLE 11-continued

| Name of Factors | Corresponding Diseases |
| --- | --- |
| Interleukin 17B (IL17B) | Laryngeal squamous cell carcinoma, multiple myeloma, non-small cell lung cancer, gastric cancer, childhood asthma, colon cancer, pancreatic cancer |
| Interleukin 20 (IL20) | Allergic rhinitis, chronic obstructive pulmonary disease, psoriasis, rheumatoid arthritis, bronchial asthma, lichen planus, unstable angina, acute coronary syndrome, periodontitis |
| Growth differentiation factor 3 (GDF3) | Prostate cancer, breast cancer, teratocarcinoma, embryonal carcinoma |
| Macrophage migration inhibitory factor (glycosylation-inhibitory factor) (MIF) | Ovarian cancer, coronary heart disease, atherosclerosis, atopic dermatitis, endometrial cancer, cerebral infarction, acute pancreatitis, cervical squamous cell carcinoma, gastric cancer, colorectal cancer, rheumatoid arthritis, oral squamous cell carcinoma, liver cancer, colon cancer, non-small cell lung cancer, diabetes, nasopharyngeal carcinoma, bladder cancer, esophageal squamous cell carcinoma |
| Bone morphogenetic protein (BMP) | Brain glioma, liver cancer, colorectal cancer |
| Thrombopoietin (THPO) | Acute cerebral infarction, primary Sjogren's syndrome, childhood aplastic anemia, aplastic anemia, hypertension, coronary heart disease, cerebral palsy, neonatal hypoxic-ischemic encephalopathy, hepatitis B |
| kallikrein-related peptidase 15 (KLK15) | Prostate cancer, ovarian cancer, thyroid cancer, breast cancer, celiac disease, childhood leukemia |
| Leukotriene C4 synthase (LTC4S) | Ischemic stroke, asthma, obstructive sleep apnea hypopnea syndrome, lupus erythematosus, cardiovascular disease |
| Chemokine (C-C motif) ligand 2 (CCL2) | Parkinson's disease, breast cancer, leukemia, prostate cancer, hypoxic-ischemic brain damage, colorectal cancer, hepatocellular carcinoma, gout, tonsillitis, gastric cancer, acute respiratory distress syndrome, type-2 diabetes, coronary heart disease, obsessive compulsive disorder, rheumatoid arthritis, knee osteoarthritis, chronic kidney disease, ischemic stroke, nonalcoholic fatty liver disease |
| Interleukin 6 (IL6) | Heart failure disease; pulmonary infection; metabolic syndrome; type-2 diabetes; coronary heart disease; fatty liver; neonatal sepsis; hand-foot-and-mouth disease; chronic obstructive pulmonary disease; liver cancer; rheumatoid arthritis; hepatitis B; transient ischemic attack; cervical cancer; acute coronary syndromes; endometrial cancer; lung cancer; ischemic stroke; prostate cancer; lupus erythematosus; esophageal squamous cell carcinoma; multiple sclerosis; dermatomyositis; nasopharyngeal carcinoma; cardiovascular disease; prostate cancer, inflammatory diseases of the nervous system |
| Interleukin 10 (IL10) | Inflammatory bowel disease; rheumatoid arthritis; psoriasis; gastric cancer; coronary heart disease; periodontal disease; cardiovascular disease; asthma; type-1 diabetes; schizophrenia; chronic obstructive pulmonary disease; sepsis; atopic dermatitis; type-2 diabetes; acute coronary syndrome; hepatitis B; lupus erythematosus; hand-foot-and-mouth disease; encephalitis; cervical cancer; eclampsia; tuberculosis |
| Interferon (α) receptor 2 (IFNAR2) | Hepatitis C, hepatitis B |
| Platelet derived growth factor A (PDGFA) | Hilar cholangiocarcinoma, systemic sclerosis, colorectal cancer, ulcerative colitis, cervical squamous cell carcinoma, nasopharyngeal carcinoma |
| Platelet derived growth factor C (PDGFC) | Breast cancer |
| Platelet derived growth factor D (PDGFD) | Breast cancer, gastric cancer, colorectal cancer, liver cancer, coronary heart disease, diabetic macrovascular complications cholangiocarcinoma, esophageal squamous cell carcinoma, coronary atherosclerotic heart disease, ovarian cancer, cerebral hemorrhage, prostate cancer, ischemic stroke |
| C-reactive protein (CRP) | Childhood pneumonia, chronic obstructive pulmonary disease, coronary heart disease, asthma, polycystic ovary syndrome, hypertension, obstructive sleep apnea hypopnea syndrome, neonatal sepsis, depression, Kawasaki disease, community-acquired pneumonia, diabetes nephropathy, rheumatoid arthritis, type-2 diabetes, cerebral infarction, pancreatitis, sepsis, colon cancer, schizophrenia, renal cell carcinoma, myocardial infarction, atherosclerosis, cerebrovascular disease, ischemic cardio-cerebrovascular disease, metabolic syndrome |

TABLE 11-continued

| Name of Factors | Corresponding Diseases |
|---|---|
| kallikrein-related peptidase 4 (KLK4) | Endometrial cancer, breast cancer, ovarian cancer, colorectal cancer |
| kallikrein-related peptidase 5 (KLK5) | Breast cancer, colorectal adenocarcinoma, rectal cancer, ovarian cancer, Netherton's syndrome, atopic dermatitis |
| Bradykinin receptor B1 (BDKRB1) | Cervical cancer, bladder cancer, endometrial cancer, gallbladder cancer |
| Interleukin α6 (IFNA6) | Hepatitis B |

Example 9 Synergistic Effect of Algal Proteoglycan Extract in Combination With Chemotherapeutic Agents on the Treatment of Cancer The experimental animals used in this study were female C57 mice (18-22 g) or female KM mice (18-22 g), which were provided by Shanghai Experimental Animal Center of the Chinese Academy of Sciences, Certificate No.: 005.

Tumors, including B-16 melanoma and S-180 sarcoma, were provided by Shanghai Institute of Materia Medica of the Chinese Academy of Sciences.

Carboplatin was purchased from Shandong Qilu Pharmaceutical Factory. Adriamycin was purchased from Zhejiang Haimen Pharmaceutical Factory. Etoposide was purchased from Pudong Pharmaceutical Factory of Yadong Pharmaceutical Company of Shanghai Pharmaceutical Industry Research Institute. 5-fluorouracil was purchased from Shanghai Xudong Haipu Pharmaceutical Co., Ltd. Cyclophosphamide was purchased from Shanghai Hualian Pharmaceutical Co., Ltd. The rest chemotherapy drugs were purchased from Beijing Kerui Biological Engineering Co., Ltd.

Example 9.1 Therapeutic Effect of Algal Proteoglycan Extract in Combination With Other Chemotherapeutic Agents on Melanoma Experimental Scheme Female C57 mice (18-22 g) and well-grown B16 melanoma on 7-11 days were used. The tumor tissue was made into cell suspension. The mice were inoculated subcutaneously in the right axilla with the cell suspension, about $4.5\text{-}5\times10^6$ cells/mouse. After 24 hours, the mice were randomly divided into different groups and housed in separate cages (n=6). Algal proteoglycan extract was administered orally, and carboplatin, doxorubicin or CTX were administered intraperitoneally, once a day. The administration began on the second day and lasted for seven days, with different doses. The blank control group was given normal saline (NS). The animals were sacrificed and weighed (g body weight) 24 hours after drug withdrawal. The tumors were excised and weighed. The average tumor weight was calculated for each group. According to the following formula, the tumor inhibition rate was calculated and T test was conducted.

$$\text{Tumor inhibition rate} = \frac{A - B}{A} \times 100\%$$

A=average tumor weight (g) of blank control group,
B=average tumor weight (g) of therapeutic group
Dosage According to the results of preliminary experiments, the dose of algal proteoglycan extract (hereinafter referred to as algal proteoglycan) was set at 30 mg/kg and 60 mg/kg, the doses of carboplatin were 4 mg/kg and 8 mg/kg, the dose of doxorubicin was 1 mg/kg, and CTX was administered at 7.5 mg/Kg.

Experimental Results

TABLE 12

Therapeutic Effect of Algal Proteoglycan (30 mg/kg) Combined with Carboplatin on Melanoma

| Group | Dose | Route of Administration | Number of Animals | | Body Weight (g) | | Tumor Weight (g) x ± SD | Tumor Inhibition Rate (%) | P Value |
|---|---|---|---|---|---|---|---|---|---|
| | | | in the Beginning | in the End | in the Beginning | in the End | | | |
| NS | — | | 20 | 20 | 17.8 | 18.9 | 1.49 ± 0.50 | — | — |
| Carboplatin | 4 mg/kg | i.p | 10 | 9 | 18.0 | 16.7 | 1.07 ± 0.88 | 28.2 | >0.05 |
| Algal proteoglycan | 30 mg/kg | p.o | 10 | 10 | 17.9 | 17.5 | 1.30 ± 0.65 | 12.8 | >0.05 |
| Carboplatin + Algal proteoglycan | 4 mg + 30 mg/kg | i.p + p.o | 10 | 10 | 17.6 | 18.1 | 0.91 ± 0.62 | 38.9 | <0.01 |

TABLE 13

Therapeutic Effect of Algal Proteoglycan (60 mg/kg) Combined with Carboplatin on Melanoma

| Group | Dose | Route of Administration | Number of Animals | | Body Weight (g) | | Tumor Weight (g) x ± SD | Tumor Inhibition Rate (%) | P Value |
|---|---|---|---|---|---|---|---|---|---|
| | | | in the Beginning | in the End | in the Beginning | in the End | | | |
| NS | — | | 20 | 18 | 20.5 | 23.7 | 1.43 ± 0.51 | — | — |
| Carboplatin | 4 mg/kg | i.p | 10 | 9 | 20.3 | 23.2 | 1.23 ± 0.37 | 14.0 | >0.05 |

TABLE 13-continued

Therapeutic Effect of Algal Proteoglycan (60 mg/kg) Combined with Carboplatin on Melanoma

| Group | Dose | Route of Administration | Number of Animals in the Beginning | Number of Animals in the End | Body Weight (g) in the Beginning | Body Weight (g) in the End | Tumor Weight (g) x ± SD | Tumor Inhibition Rate (%) | P Value |
|---|---|---|---|---|---|---|---|---|---|
| Algal proteoglycan 60 mg/kg | | p.o | 10 | 10 | 20.5 | 22.6 | 1.00 ± 0.36 | 30.1 | <0.01 |
| Carboplatin + Algal proteoglycan 60 mg/kg | 4 mg + | i.p + p.o | 10 | 9 | 20.5 | 23.3 | 0.85 ± 0.50 | 40.6 | <0.01 |

TABLE 14

Therapeutic Effect of Algal Proteoglycan Combined with Adriamycin on Melanoma

| Group | Dose | Route of Administration | Number of Animals in the Beginning | Number of Animals in the End | Body Weight (g) in the Beginning | Body Weight (g) in the End | Tumor Weight (g) x ± SD | Inhibition Rate (%) | P Value |
|---|---|---|---|---|---|---|---|---|---|
| NS | — | | 40 | 40 | 20.6 | 26.4 | 3.37 ± 1.27 | — | — |
| Adriamycin | 1 mg/kg | i.p | 10 | 10 | 20.8 | 24.8 | 1.97 ± 0.84 | 41.5 | <0.01 |
| Algal proteoglycan | 30 mg/kg | p.o | 10 | 10 | 20.5 | 25.4 | 2.84 ± 0.80 | 15.7 | >0.05 |
| Adriamycin + Algal proteoglycan 30 mg/kg | 1 mg + | i.p + p.o | 10 | 10 | 20.7 | 23.2 | 1.53 ± 0.54 | 54.6 | <0.01 |

The above results showed that, compared with the monotherapy, the antitumor effect of algal proteoglycan combined with carboplatin or doxorubicin was significantly enhanced, but the toxicity was not increased. Taking algal proteoglycan at a dose of 30 mg/kg for example, although algal proteoglycan (30 mg/kg) did not effectively inhibit melanoma growth alone (P>0.05), it can significantly enhance the effect of other antitumor drugs. For example, when algal proteoglycan (30 mg/kg) was used in combination with carboplatin, the antitumor effect of carboplatin was significantly increased (with tumor inhibition rate being 38.9%), compared to the monotherapy of carboplatin (P<0.01). When algal proteoglycan (30 mg/kg) was used in combination with doxorubicin, the tumor inhibition rate of doxorubicin was significantly increased by 13.1%. When carboplatin was combined with algal proteoglycan (60 mg/kg), the inhibition rate of carboplatin was significantly increased by 26.6%.

The above results show that the algal proteoglycan extract disclosed herein can enhance the therapeutic effect of chemotherapeutic agents such as carboplatin and doxorubicin on transplanted tumor of B16 melanoma in mice, demonstrating that the algae proteoglycan extract and the commonly-used chemotherapeutic agents have a synergistic effect in the treatment of melanoma.

Example 9.2 Therapeutic Effect of Algal Proteoglycan Extract in Combination With Other Chemotherapeutic Agents on S-180 Sarcoma in Mice Experimental Scheme Female KM mice (18-22 g) and well-grown S-180 melanoma on 7-11 days were used. The tumor tissue was made into cell suspension. The mice were inoculated subcutaneously in the right axilla with the cell suspension, about 4.5-5×10⁶ cells/mouse. After 24 hours, the mice were randomly divided into different groups and housed in separate cages (n=6). Algal proteoglycan extract (hereinafter referred to as algal proteoglycan) was administered orally; and cyclophosphamide, carboplatin, 5-fluorouracil and etoposide were administered intraperitoneally, once a day. The administration began on the second day and lasted for seven days, with different doses. The blank control group was given normal saline (NS). The animals were sacrificed and weighed (g body weight) 24 hours after drug withdrawal. The tumors were excised and weighed. The average tumor weight was calculated for each group. According to the following formula, the tumor inhibition rate was calculated and T test was conducted.

According to the formula below, the tumor inhibition rate was calculated and T test was conducted.

$$\text{Tumor inhibition rate} = \frac{A - B}{A} \times 100\%$$

A=average tumor weight (g) of blank control group,
B=average tumor weight (g) of therapeutic group Experimental Results

TABLE 15

Therapeutic Effect of Algal Proteoglycan Combined with Cyclophosphamide on S-180 Sarcoma in Mice

| Group | Dose | Route of Administration | Number of Animals in the Beginning | Number of Animals in the End | Body Weight (g) in the Beginning | Body Weight (g) in the End | Tumor Weight (g) x ± SD | Tumor Inhibition Rate (%) | P Value |
|---|---|---|---|---|---|---|---|---|---|
| NS | — | | 20 | 19 | 22.7 | 25.5 | 1.92 ± 0.51 | — | — |
| Cyclophosphamide | 7.5 mg/kg | i.p | 10 | 10 | 22.8 | 24.9 | 1.11 ± 0.24 | 42.2 | <0.01 |
| Algal proteoglycan | 60 mg/kg | p.o | 10 | 9 | 23.0 | 23.4 | 1.24 ± 0.49 | 35.4 | <0.01 |
| Cyclophosphamide + algal proteoglycan | 7.5 mg + 60 mg/kg | i.p + p.o | 10 | 9 | 22.9 | 25.4 | 0.91 ± 0.23 | 52.6 | <0.01 |

TABLE 16

Therapeutic Effect of Algal Proteoglycan Combined with Carboplatin on S-180 Sarcoma in Mice

| Group | Dose | Route of Administration | Number of Animals in the Beginning | Number of Animals in the End | Body Weight (g) in the Beginning | Body Weight (g) in the End | Tumor Weight (g) x ± SD | Tumor Inhibition Rate (%) | P Value |
|---|---|---|---|---|---|---|---|---|---|
| NS | — | | 30 | 30 | 18.7 | 30.4 | 1.82 ± 0.69 | — | — |
| Carboplatin | 4 mg/kg | i.p | 10 | 10 | 18.6 | 26.4 | 1.68 ± 0.53 | 7.7 | >0.05 |
| Algal proteoglycan | 20 mg/kg | p.o | 10 | 10 | 18.7 | 27.8 | 1.75 ± 0.48 | 3.8 | >0.05 |
| Carboplatin + algal proteoglycan | 4 mg + 20 mg/kg | i.p + p.o | 10 | 10 | 18.8 | 24.7 | 1.22 ± 0.54 | 33.0 | <0.05 |

TABLE 17

Therapeutic Effect of Algal Proteoglycan Combined with Etoposide on S-180 Sarcoma in Mice

| Group | Dose | Route of Administration | Number of Animals in the Beginning | Number of Animals in the End | Body Weight (g) in the Beginning | Body Weight (g) in the End | Tumor Weight (g) x ± SD | Tumor Inhibition Rate (%) | P Value |
|---|---|---|---|---|---|---|---|---|---|
| NS | — | | 30 | 30 | 18.7 | 30.4 | 1.82 ± 0.69 | — | — |
| Etoposide | 3 mg/kg | i.p | 10 | 10 | 18.7 | 25.7 | 1.33 ± 0.28 | 26.9 | >0.05 |
| Algal proteoglycan | 20 mg/kg | p.o | 10 | 10 | 18.7 | 27.8 | 1.75 ± 0.48 | 3.8 | >0.05 |
| Algal proteoglycan | 30 mg/kg | p.o | 10 | 10 | 18.6 | 27.5 | 1.44 ± 0.67 | 20.9 | >0.05 |
| Etoposide + Algal proteoglycan | 3 mg + 20 mg/kg | i.p + p.o | 10 | 10 | 18.7 | 24.2 | 1.21 ± 0.41 | 33.5 | <0.05 |
| Etoposide + Algal proteoglycan | 3 mg + 30 mg/kg | i.p + p.o | 10 | 10 | 18.6 | 23.4 | 1.17 ± 0.44 | 35.7 | <0.01 |

TABLE 18

Therapeutic Effect of Algal Proteoglycan Combined with 5-Fluorouracil on S-180 Sarcoma in Mice

| Group | Dose | Route of Administration | Number of Animals in the Beginning | Number of Animals in the End | Body Weight (g) in the Beginning | Body Weight (g) in the End | Tumor Weight (g) x ± SD | Tumor Inhibition Rate (%) | P Value |
|---|---|---|---|---|---|---|---|---|---|
| NS | — | | 16 | 16 | 18.4 | 25.3 | 1.57 ± 0.51 | — | — |
| 5-Fluorouracil | 15 mg/kg | i.p | 8 | 8 | 18.6 | 22.9 | 1.04 ± 0.52 | 33.8 | <0.05 |
| Algal proteoglycan | 20 mg/kg | p.o | 8 | 8 | 18.3 | 22.4 | 1.56 ± 0.51 | 0.6 | >0.05 |
| 5-Fluorouracil + algal proteoglycan | 15 mg + 20 mg/kg | i.p + p.o | 8 | 8 | 18.3 | 21.6 | 0.51 ± 0.28 | 67.5 | <0.01 |

From the data listed in Tables 15-18, it can be seen that the algal proteoglycan at a dose of 20-30 mg/kg did not inhibit the growth of S-180 sarcoma (P>0.05), and the algal proteoglycan at a dose of 60 mg/kg inhibited growth of S-180 sarcoma with the inhibition rate of 35.4%, demonstrating an inhibitory effect of the algal proteoglycan on the growth of mouse sarcoma.

Carboplatin at a dose of 4 mg/kg used alone had no inhibitory effect on the growth of the transplanted tumor of S-180 sarcoma in mice (P>0.05). When carboplatin at a dose of 4 mg/k was used in combination with 20 mg/kg algal proteoglycan, the inhibition rate was 33%. Algal proteoglycan at a dose of 60 mg/kg used in combination with 7.5 mg/kg cyclophosphamide achieved an inhibition rate of 52.6% for the growth of S-180 sarcoma, 10% higher than the inhibition rate achieved by using cyclophosphamide alone.

The inhibitory effect on the growth of the transplanted tumor of S-180 sarcoma in mice achieved by 3 mg/kg etoposide alone was 26.9% (P>0.05). When etoposide was used with 20 and 30 mg/kg algal proteoglycan, the inhibition rate was increased to 33.5% (P<0.05) and 35.7% (P<0.01) respectively.

5-fluorouracil at a dose of 15 mg/kg used alone had a moderate inhibitory effect on the transplanted tumor of S-180 sarcoma in mice. When 5-fluorouracil was combined with algae proteoglycan, the anti-tumor effect was significantly increased with the inhibition rate of 67.5%, demonstrating that the combination of two drugs had produced a synergistic effect.

The above data showed that the combined use of the algal proteoglycan extract disclosed herein and chemotherapeutic agents such as 5-fluorouracil, etoposide, carboplatin and cyclophosphamide can increase the therapeutic efficacy of these chemotherapeutic drugs on S-180 sarcoma in mice, and the synergistic effect of algal proteoglycan combined with 5-fluorouracil is more significant.

In addition, the applicants have also studied the inhibitory effect of the algal proteoglycan extract used alone and the extract used in combination with gemcitabine on in vivo tumor in nude mice with pancreatic cancer, as well as the inhibitory effect on pancreatic carcinoma in patient-derived tumor xenograft models (PDX). The results showed that the combined use of the algal proteoglycan extract disclosed herein and gemcitabine has also a synergistic effect on the treatment of pancreatic carcinoma.

It is understood that, although the inventions has been described in some detail by way of illustration and examples, these inventions are not limited to specific details described in these specific forms. Apparently to those skilled in this field, various equivalent changes and modifications to the technical features involved in the inventions may be practiced without deviating from the spirit of the inventions described herein, and such changes and modifications are within the scope of the inventions.

What is claimed is:

1. A method for treating inflammation or diseases mediated by inflammatory factors in a subject in need thereof, comprising administering a therapeutically or prophylactically effective amount of an algal proteoglycan extract or a composition comprising a therapeutically or prophylactically effective amount of the algal proteoglycan extract to the subject.

2. The method according to claim 1, wherein the inflammation is tumor-associated inflammation.

3. The method according to claim 2, wherein the tumor is a primary tumor or a metastatic tumor.

4. The method according to claim 3, the tumor is selected from sarcoma, lymphoma, esophageal cancer, pancreatic cancer, melanoma, leukemia, lung cancer, liver cancer, gastric cancer, breast cancer, cutaneous squamous carcinoma, colon cancer, or metastatic cancers thereof.

5. The method according to claim 1, wherein the inflammatory factor is selected from one or more of the following: histamine receptor H3, kallikrein-related peptidase 3, kallikrein-related peptidase 13, insulin-like growth factor 2, tumor necrosis factor, leukotriene B4 receptor 2, chemokine (C—C motif) ligand 4, colony stimulating factor 3 (granulocyte), dopamine receptor 4, platelet-derived growth factor β polypeptide, kallikrein-related peptidase 11, kallikrein-related peptidase 15, leukotriene B4 receptor, leukotriene C4 synthase, chemokine (C—C motif) ligand 2, interleukin-6, interleukin-10, interferon-α receptor 2, platelet-derived growth factor A, platelet-derived growth factor C, platelet-derived growth factor D, C-reactive protein, kallikrein-related peptidase 14, bradykinin receptor B2, tumor necrosis factor (ligand) superfamily member 11, chemokine (C—C motif) ligand 3, chemokine (C—C motif) ligand 7, chemokine (C—C motif) ligand 20, chemokine (C—X—C motif) ligand 2, interferon (α, β and Ω) receptor 1, interleukin 3, interleukin 9, interleukin 17B, interleukin 20, growth differentiation factor 2, growth differentiation factor 3, macrophage migration inhibitory factor (glycosylation-inhibiting factor), grow differentiation factor 11, bone morphogenetic protein 2, bone morphogenetic protein 4, thrombopoietin, kallikrein-related peptidase 4, kallikrein-related peptidase 5, bradykinin receptor B1 and interferon-α6.

6. The method according to claim 1, wherein the algal proteoglycan extract and/or the algal proteoglycan extract together with a pharmaceutically acceptable carrier are formulated into pharmaceutically acceptable dosage forms.

7. The method according to claim 6, wherein the pharmaceutically acceptable dosage forms are liquids for oral administration, capsules, powders, tablets, granules, pills, syrups or injectable formulations.

8. The method according to claim 1, wherein the algal proteoglycan extract is administered orally, subcutaneously, intramuscularly or intraperitoneally.

9. The method according to claim 1, wherein the algal proteoglycan extract is administered orally.

10. The method according to claim 1, wherein the algal proteoglycan extract is administrated at a dosage of 5-500 mg/kg body weight per day.

11. The method according to claim 10, wherein the algal proteoglycan extract is administrated at a dosage of 20-150 mg/kg body weight per day.

12. The method according to claim 11 wherein the algal proteoglycan extract is administrated at a dosage of 30-120 mg/kg body weight per day.

13. The method according to claim 1, wherein the algal proteoglycan extract is obtained by the following steps:
   (a) dissolving blue-green algae powder in a 5-20 fold volume of water, and breaking the algal cell walls;
   (b) heating the resulting mixture in step (a) at 60-100° C., and performing solid-liquid separation after cooling;
   (c) adjusting the pH of the resulting liquid in step (b) to less than 7, and performing solid-liquid separation again; and
   (d) adjusting the resulting liquid in step (c) to a neutral pH, concentrating the liquid, and drying the liquid if necessary.

14. The method according to claim 13, wherein the content of proteoglycan contained in the algal proteoglycan extract is more than about 50% by weight.

15. The method according to claim 13, wherein the content of proteoglycan contained in the algal proteoglycan extract is more than about 60% by weight.

16. The method according to claim 13, wherein the content of proteoglycan contained in the algal proteoglycan extract is more than about 65% by weight.

17. The method according to claim 13, wherein the content of proteoglycan contained in the algal proteoglycan extract is more than about 70% by weight.

18. The method according to claim 13, wherein the content of proteoglycan contained in the algal proteoglycan extract is more than about 75% by weight.

* * * * *